United States Patent [19]

Harris

[11] Patent Number: 4,606,650
[45] Date of Patent: Aug. 19, 1986

[54] MICROWAVE, A CLOSED VESSEL AND METHODS OF DETERMINING VOLATILE MATERIAL CONTENT

[75] Inventor: Robert G. Harris, Montreal, Canada
[73] Assignee: Domtar Inc., Montreal, Canada
[21] Appl. No.: 674,981
[22] Filed: Nov. 26, 1984
[51] Int. Cl.⁴ .................. G01N 25/02; G01G 23/00
[52] U.S. Cl. ............................ 374/14; 177/245
[58] Field of Search ................ 374/14, 17, 157; 177/210 R, 245; 220/202, 308

[56] References Cited

U.S. PATENT DOCUMENTS

| | | | |
|---|---|---|---|
| 3,283,560 | 11/1966 | Harden et al. | 374/12 |
| 3,620,408 | 11/1971 | Holbrook et al. | 220/202 X |
| 3,717,210 | 2/1973 | Sieswerds | 177/245 X |
| 3,890,825 | 6/1975 | Davis | 374/14 |
| 3,915,336 | 10/1975 | Spreng | 220/308 |
| 4,276,462 | 6/1981 | Risman | 219/10.55 F |
| 4,291,775 | 9/1981 | Collins | 177/1 |
| 4,485,284 | 11/1984 | Pakulis | 374/14 |

OTHER PUBLICATIONS

"Thermal Analysis in Corrosive Gas Atmospheres", Mettler Ins. Corp., Tech. Bulletin T-103, 4 pages, 3/3/67.

*Primary Examiner*—Daniel M. Yasich

[57] ABSTRACT

A microwave vacuum oven for quickly removing volatile material from laboratory samples: The oven has a vacuum chamber for receiving the samples in a closed vessel and a vacuum source for expelling volatile material. This vessel has preferably a deformable gasket for sealing engagement with a top and bottom portion, and a gas passage is also provided therein for easily removing the top portion. Auxiliary components are also disclosed for gradually decreasing the microwave energy output in accordance with residual volatile material present at a given time in a system. A method described includes (a) maintaining a vacuum environment around a sample containing volatile material, (b) subjecting the sample to microwave radiation energy, to rapidly liberate its volatile material while measuring the rate of volatilization of the sample over time, (c) detecting the point at which said rate of volatilization decreases, (d) at said point decreasing the amount of radiation energy generated into said sample, while maintaining vacuum and continuing detecting the rate of volatilization, until said rate stops, indicative that said volatile material is completely liberated from said sample, and (e) stopping the radiation at or near the point at which said volatile material is completely liberated from said sample while said vacuum is maintained until the environment surrounding said sample is substantially free from any volatile material liberated from said sample.

12 Claims, 2 Drawing Figures

MICROWAVE, A CLOSED VESSEL AND METHODS OF DETERMINING VOLATILE MATERIAL CONTENT

FIELD OF THE INVENTION

This invention relates to a microwave vacuum oven intended for the rapid removal of volatile material and to a method of using same. More particularly this invention relates to a microwave oven which can rapidly determine the volatile content of material or alternatively the bulk density of material and the like while minimizing the pyrolysis, the decomposition or further degeneration of the material to be tested, to a particular closed vessel and to a method for carrying out same.

BACKGROUND OF THE INVENTION

Water content in a product has been determined over decades by using a hot air oven slightly above 100° C. to expel water. The product, whose water content is to be determined, is simply left in the drying oven until the product reaches an "oven dry" state where no more weight variation is obtained. The difference between the weight of the sample before drying known to those in the art as the "green" sample, and the weight after drying is equal to the weight of the water lost. Determination of what is referred to as bulk density involves the mass of the dry sample per unit volume of "green" sample.

The period of time to allow complete exhaustion of the water from a sample is determined empirically, thus permitting a sample to be dried during a known time period to insure complete water removal. This method which requires one or two days, is time consuming and does not allow rapid moisture content determination.

A more rapid determination of moisture content using a microwave oven for drying is described in Forest Products Journal 32(10) p. 56 to 58, 1982), which hereinafter is referred to as the "Journal".

The determination of the moisture content as described in the Journal, consists of placing a sample in a microwave oven, turning on the power for various intervals, and determining weight at each interval, until the sample becomes constant in weight.

With such a method, it is difficult to thoroughly dry the material without initiation of combustion. In a conventional oven, the samples reach an oven-dry state and maintain this equilibrium with continued exposure. In a microwave oven, however, extended exposure beyond the oven-dry state results in the superheating of the centre of the sample and smoldering and smoking of the wood causing unpleasant odors and degradation of material. This introduces error in the moisture content determination and a fire hazard.

BRIEF DESCRIPTION OF THE PRESENT INVENTION

The object of the present invention is to accelerate volatile material liberation from a sample, to eliminate these weight determinations at various intervals and, preferably to reduce the danger of overheating the samples as indicated hereinabove.

Broadly stated, the invention comprises; a microwave vacuum oven for quickly removing volatile material from laboratory samples comprising in combination: a vacuum chamber for receiving at least one sample to be tested, and in combination therewith, a microwave source for expelling volatile material from said at least one sample to be tested in said vacuum chamber, a means associated with said chamber for alternatively selecting a vacuum in said chamber and for releasing from said chamber said vacuum, and thereby to quickly release volatile material from said at least one sample.

The invention also comprises; a closed vessel to be subject to conditions of microwave radiation and vacuum for carrying out tests on volatile materials, said vessel having top and bottom portions and a gas passage means for linking the interior of said vessel with the outside and each of said portions having walls susceptible to microwave radiation to liberate volatile materials from laboratory samples containing said volatile materials to be located within said vessel, said walls defining near the edges matching complementary lips for receiving the lips of the other of said portions, a deformable gasket in sealing engagement between the complementary matching lips of said top and bottom portions, to form therewith a substantially leakproof chamber provided with a passage means for gas and wherein said top portion is easily removable from said bottom portion.

The invention is also directed to a method for quickly determining the volatile material content of a laboratory sample comprising (a) subjecting a laboratory sample containing volatile material to microwave radiation energy, to rapidly liberate the volatile material in said sample, and thereafter, (b) precluding said sample from said environment containing said volatile material. The step (b) may be performed inter alia by stopping the radiation at or near the point at which said volatile material is completely liberated from said sample while maintaining said vacuum until the environment surrounding said sample is substantially free from any volatile material liberated from said sample. Another way of carrying out step (b) involves removing said sample from said environment.

By "volatile material" throughout the disclosure and the claims is meant generally organic and inorganic materials susceptible to be liberated in a gaseous state from a sample through volatilization, sublimation, evaporation, etc at a given temperature and without substantially effecting otherwise the the nature of said sample or volatile material; the term excludes, in general, those compounds which are susceptible to violent liberation of gaseous materials as is known to those skilled in the art. Along with the measurement of volatile material content, the bulk density may be obtained following the drying of samples in the microwave oven.

BRIEF DESCRIPTION OF THE DRAWING

Further features, objects and advantages will be evident in the following detailed description of the preferred embodiment of the present invention, taken in conjunction with the accompanying drawings in which.

DESCRIPTION OF THE PREFERRED EMBODIMENTS

Figure 1:
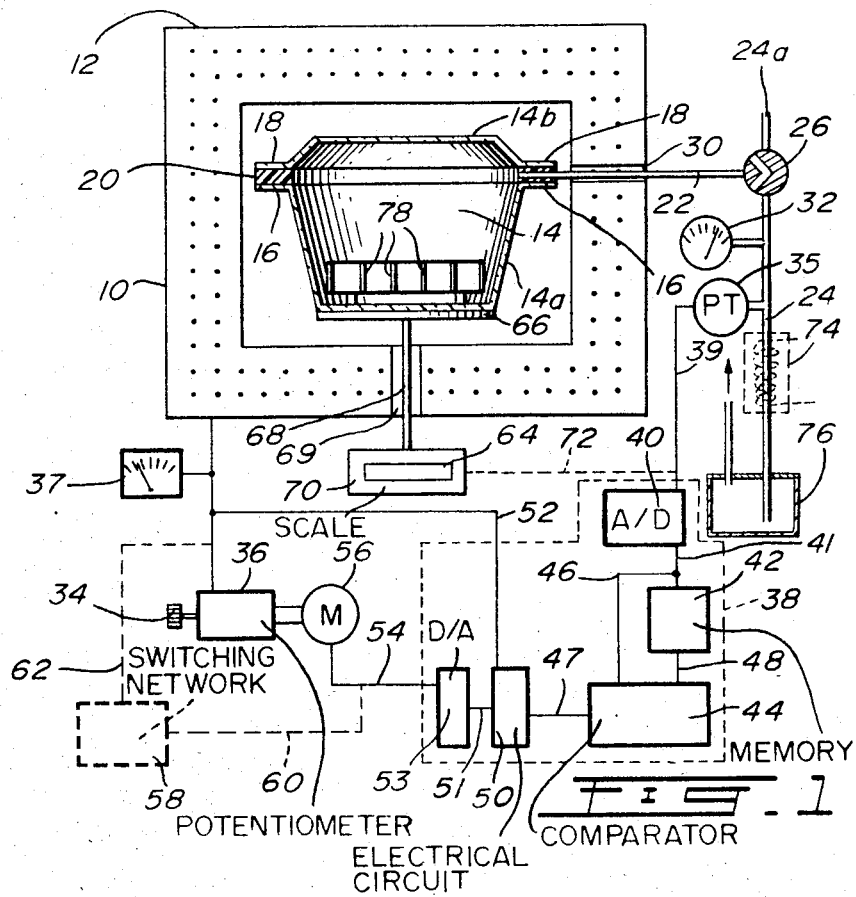
FIG. 1 is a schematic view of a microwave vacuum oven illustrating a preferred way of carrying out the invention.

Referring now to FIG. 1, the microwave vacuum oven 10 comprises a microwave oven schematically shown at 12 surrounding a closed vessel 14 which has a bottom portion 14a and a top portion 14b, said bottom and top portions having respectively, lips 16 and 18 defining complementary matching portions, and a deformable gasket 20 for sealing engagement between lips 16 and 18, such a deformability providing the mechanism for sealing under the conditions at which the invention is carried out. The gasket 20 has a thickness such as to allow for a passage for the line 22 to be in contact with the inside of the closed vessel 14. Alternatively, gasket 20 defines an air passage to which is connected line 22. The line 22 is flexible thereby moveable along with the displacement of a weight plate 66 as will be disclosed hereafter.

A further alternative involves a gas passage located in the wall of the top or bottom portions of the vessel instead of the passage through gasket 20.

Preferably gasket 20 is a thick deformable seal which enables easy removal of the top portion without having to hold the bottom portion, when the vessel, preferably a tempered glass material, is subjected to vacuum. Said thickness of gasket 20 preferably ranges from 0.5 centimeters to 2 centimeters, depending on the nature of vacuum passage chosen. It may however be a few millimeters or thicker, if desired. The gasket is also substantially inert to microwave radiation: Conveniently the gasket is made up of a polytetrafluoroethylene such as "Teflon" (a trademark for such a polymer which is commonly available).

Other materials, which are substantially not attacked by microwave radiations and which allow these radiations to reach the samples to be tested, are also contemplated for the fabrication of the gasket 20 and the vessel 14. Such materials must, however, withstand the vacuum in the case of the vessel and have lubricatory properties to ease removal in the case of the seal.

The vessel 14 must also be "susceptible to microwave radiations: that is, it must respond to allow microwave radiation to a sample located in the closed vessel, and preferably maximized microwave radiation into said sample as will be discussed hereinbelow.

When the microwave radiation source is outside the vessel, the words "susceptible to microwave radiations" in relation to the walls of the vessel means that at least a portion of the walls of the vessel are substantially not absorbing microwave radiation to allow the passage or the transmission of the radiation to said sample. The remaining portion of the walls may, if desired, be reflective of said microwave radiation to maximize heat radiation.

The line 22 is connected to a vacuum line 24, as is well known and generally present in laboratories, and is provided with a valve 26 for allowing air into the vessel 14 when desired. Other means such as pumping means may also be used to create vacuum, if desired.

The microwave oven, is conveniently provided with a small aperture 30 to enable the passage of flexible line 22 outside said oven, while minimizing the microwave radiation outside the oven.

SOME OF THE WAYS OF OBTAINING VARIABLE MICROWAVE ENERGY OUTPUT

There are various ways of obtaining variable energy output such as by alternating or pulsating currents, or by varying the energy output according to a sensing device which measures the degree of dryness of a sample or of gases which have been liberated.

Preferably, the vacuum of the vessel is measured, such as by vacuum gauge 32.

The oven is also equipped with an adjusting means 34, to operate a potentiometer 36 or a pulsating device to regulate the current or voltage, or by other means to allow variable microwave energy output. The said output is registered on display 37, said display preferably of the digital or analogue type.

In another embodiment, a vacuum sensing device such as a gauge or pressure tranducer or other suitable vacuum measuring devices, as shown at 35, conveys the information, an analog signal pertaining to the vacuum, to the "analog to digital" converter 40 of control unit 38 by means of conductor 39.

The control unit 38 consists of an "analog to digital" converter 40, a memory device 42 to receive and store digital signals from conductor 41 pertaining to said vacuum from the said converter 40, comparator 44 to evaluate change in said vacuum level by comparing present vacuum signal on conductor 41, 46 with past vacuum signal on conductor 48 conveyed by memory device 42. An electrical circuit 50 detects the signal conveyed by conductor 52, representing present microwave output level, and determines necessary adjustments of potentiometer 36 based on the vacuum change, over a preset period of time, conveyed by conductor 47. A "digital to analog" converter 53 translates to an analog signal received on line 54, the digital signal conveyed on conductor 51 from said electrical circuit 50. Thus, the control unit 38, conveying the signal by conductor 54 to servomotor 56, controls potentiometer 36. Instead of a servomotor for adjusting the potentiometer, a solenoid may be used if desired. Also, instead of the vacuum sensing device 35, a temperature sensing device may be used, if desired though less preferred, or a combination thereof.

Still in another embodiment, instead of the servomotor 56, an alternataive means of controlling microwave energy output is shown in dotted lines, which involves, inter alia, a switching network 58. Thus, the control unit 38 conveys a signal by conductor 64, 60 to the switching network 58, which is operatively connected to select one of several preset microwave output energy levels based on the vacuum level changes, and conveys the preset energy level to the microwave oven 12 via conductor 62.

Instead of a vacuum device 35, a weigh scale 64 measuring the weight of the vacuum chamber 14 and content therein may be used to obtain variable microwave energy output. In such a case, generally a single sample is dried when such a scale is used. The weight scale which measures the degree of dryness of the sample has a base 66 located inside the oven 12 on which is placed vacuum chamber 14. The base is susceptible to microwave radiation, that is, the base is inert to microwave radiation and is substantially not absorbing microwave radiation. A rigid link 68 is connected to base or plate 66 and passes through normally a small aperture 69 to transmit the weight exerted by chamber 14 to a weight measuring scale or balance 70 provided with a calibrated spring, or other calibrated device (not shown) as is well known, and located outside the oven to prevent exposure to microwave radiation. The weight measuring scale 70 conveys a signal via conductor 72 to conductor 39 to be monitored by control unit 38, the same way which has been discussed with pressure transducer 35 to produce the necessary adjustments to the microwave energy output.

The weight measuring scale 70 may also be positioned inside the microwave oven 12, if desired, provided said scale 70 is surrounded with a material reflecting microwave radiations, as is known to those skilled in the art.

Instead of electrical components for the automatic control and adjustment means of the microwave oven disclosed above, functionally equivalent mechanisms involving pneumatic and hydraulic components are also contemplated.

Although reference has been made to a vacuum oven with a vessel 14 surrounded by a microwave source, the vessel 14 may instead contain therein the radiation source, and in such a case the walls constituent of the vessel would preferably be such as to reflect microwave radiation as is known in the art, and the word "susceptible" is intended in such a circumstance to imply those characteristics.

In another embodiment, the vacuum line 24 is passed through a condenser 74 to condense a liberated volatile material having low partial pressure and is collected in container 76 to be volumetrically or gravimetrically measured. The rate of volatile material collection in container 76 then equals the rate at which volatile material is expelled from said samples contained in open sample containers 78. During a drying process, the rate of volatile material collection in the container 76 will increase and remain substantially constant, reflecting a steady "radial" flow of volatile material from the innermost region of the sample to its exposed periphery of the sample where it liberates to the vacuum chamber. As the drying process nears its completion, this "radial" flow within the sample is reduced, thereby reducing the accumulation rate of the volatile material condensate. This decrease would trigger a decrease in microwave energy output. Further modifications to microwave energy output with decreasing accumulation rate would be determined empirically.

When one manually operates the oven, or when an unknown sample is used, the following may be used. Before carrying out tests, the vessel is assembled and valve 26 closed to the outside and turned to the vacuum of line 24 pumps out the air. The needle of the vacuum gauge 32 or other means indicates the approximate maximum vacuum that system has reached. This value is noted as "approximate maximum vacuum". The valve 26 is then opened to release the vacuum and the top 14b of the vessel is easily removed.

When one wishes to determine the volatile content of a material, samples may be weighed. The top 14b of the vessel 14 is then easily removed without having to force or slide the top portion 14b with difficulty. This is often the case when a vessel, having a cover, has been subjected to vacuum.

By easing the removal of the top 14b, the gasket 20 further allows the bottom portion 14a to remain in the oven with the gasket thereupon connected to vacuum line 22, thereby further saving time to operate.

The sample, or samples as the case may be, are then introduced and the top 14b replaced on. The vacuum is started ensuring that the valve 26 is turned to be closed to the outside (24a), and the potentiometer 36 is adjusted generally to the full position. The gauge 32 indicates a gradually reduced vacuum up to a point, where it remains constant, indicative that most of the volatile materials have left the samples. The potentiometer is then decreased until the vacuum reaches the "approximate maximum value", as determined hereinabove.

The container or containers 78 may then be weighed and the volatile content determined as it is well known to those skilled in the art.

The heat to be delivered when most of the volatile materials have left the samples, as determined by the gauge or other sensing devices, is preferably slightly in excess of that required to remove all the volatile materials in the vessel.

One method, to automatically control the microwave energy output, involves obtaining the "approximate maximum vacuum", knowing the nature and the size of the sample (or samples) to be tested, and the energy output of the microwave. One can thereby elaborate a gradually uniformly or step decreasing energy output, to be such as to supply energy output slightly in excess of that required, at a point in time, to carry out the removal of volatile materials which are removable at that point in time, and thereby to prevent over-heating of the sample.

In another method, updates are made of: (a) the vacuum level with vacuum sensing devices 35, (b) the temperature level with suitable temperature sensing devices, or (c) the weight of the vessel 14 with weigh scale 64 to determine the degree to which the volatile materials have been removed from the sample. Corresponding adjustments are then made on the potentiometer 36, thereby regulating the microwave energy output. In the case of vacuum measurement, the partial pressure exerted by the liberated volatile material in vessel 14 causes the vacuum level to decrease with respect to time. The vacuum level then reaches a minimum or a plateau, with respect to time, when the rate of volatile material liberated from the sample equals the rate of volatile removal from the vessel 14. At such a point the control unit 38 reduces the microwave energy output, until complete liberation of the volatiles occurs in the vessel identified by a vacuum level equal to the "approximate maximum vacuum". The microwave energy output is then terminated. In the case of temperature measurement, a plateau with respect to time is obtained at the beginning of the drying procedure. As soon as the temperature starts to climb, the microwave energy output is allowed to gradually decrease until the temperature level reaches a predetermined maximum value. At this point, the microwave energy output is terminated. This predetermined temperature maximum value depends on the variables: sample weight, energy output, operable vacuum, and nature of the sample. In the case of weight measurement, a plateau is obtained as in the vacuum measurement. Following the termination of the microwave energy output, the operator releases the vacuum and removes the top portion 14b from the vessel 14. The open sample containers 78 are then removed from the vessel 14 and the dry weights measured. The determination of volatile material content can then be determined by those skilled in the art.

As already indicated, instead of the vacuum sensing device, a temperature or weight sensing device, and in some circumstances a combination thereof, may be used to identify the completion of the volatile material liberation process: (e.g. a volatile material in a highly thermolabile sample.)

During the use of the weight sensing device, care should be taken when several open sample containers 78 are present that they contain substantially the same amount of volatile material in order to deliver the "tailored" appropriate energy to all the samples.

The following examples will serve to illustrate some aspect of the nature of the invention and of the accuracy of the results obtained.

EXAMPLES 1-6

From a large amount of wood chips which had been previously well mixed to ensure homogeneity, 12 portions of 200 grams each were weighed, and 6 of those portions were used in the following manner.

In an apparatus as described hereinabove in FIG. 1 and provided with a vacuum gauge for measuring purpose, one of the 6 portions was dried, using a microwave oven drawing 13 amperes to produce 700 watts energy output at a frequency of 2450 Megahertz. The vessel was evacuated to 7 centimeters of mercury by means of a conventional water eductor (venturi type).

The vacuum gradually decreased to a minimum value of 32 to 34 centimeters of mercury pressure (also known as absolute pressure) and then increased to 25 centimeters of mercury pressure. The microwave energy output level was then adjusted to produce about 350 watts until the pressure fell to 12 centimeters of mercury pressure at which time the energy output was terminated. The time to carry out this method was about 20 to 40 minutes according to the water content of the samples.

Results from the experiments performed on the 6 samples, as illustrated in Table 1.

During these experiments, the rate at which vacuum was created remained the same. Microwave energy output was adjusted:

(a) by supplying, first a maximum amount of microwave energy output until a peak in the rate of volatile material liberation was reached, then
(b) the microwave energy output was reduced to further the volatile material liberation process near but prior to complete volatilization, and then no more energy was supplied,
(c) the volatilization being completed solely by the vacuum and the energy contained in the system.

The points at which the steps (b) and (c) are conducted were empirically determined.

SAMPLES A to F

The other six portions of wood chips were dried using a conventional hot air oven operating at 105° C. for 24-48 hours. The results from the experiment performed on these 6 samples, using the conventional hot air oven are also shown in Table 1.

As can be seen from Table 1, the microwave vacuum system results agree to within 0.4% of the results from the conventional hot air oven. Time savings by using the microwave vacuum system are substantial, ranging from 50 to 100 times. (20 to 40 mintues as compared to 1 or 2 days!)

TABLE 1

| MOISTURE CONTENT - DRIED SOLIDS (% O.D.) | | |
|---|---|---|
| MICROWAVE/ VACUUM OVEN DRIED | INDEPEN- DENT SAMPLES | CONVEN- TIONAL HOT AIR OVEN DRIED |
| Example 1  64.4 | A | 63.8 |
| 2  64.2 | B | 63.8 |
| 3  64.6 | C | 63.2 |
| 4  63.9 | D | 63.8 |
| 5  63.6 | E | 64.5 |
| 6  64.2 | F | 63.8 |
| Mean Value Examples  64.2 | 6 Samples | 63.8 |
| Standard Deviation  0.4 | | 0.4 |

EXAMPLES 7-11

The same was repeated as in Examples 1-6 except that five samples having various amounts of water were used. In the case of these samples when the minimum vacuum was below 25 centimeters of mercury, the microwave energy output level was reduced to lower energy output immediately upon reaching said minimum vacuum level.

Figure 2:
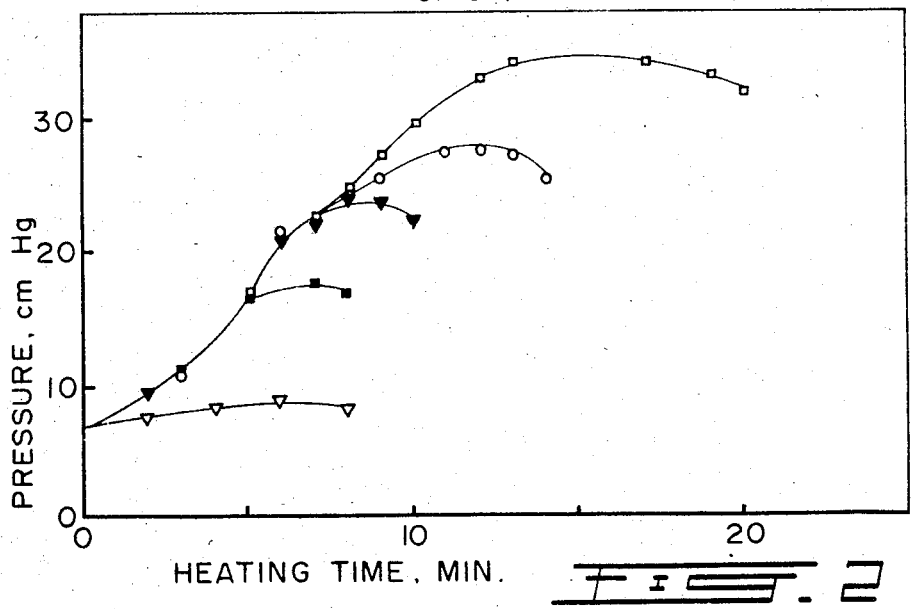
FIG. 2 is a diagram illustrating the time required to remove volatile material in samples having various levels of such volatile materials (abscissa), and the impact upon the vacuum (ordinate) at constant heating rate.

A plot of the pressure versus time was made for each and are shown on FIG. 2 to illustrate the behavior in water liberation.

EXAMPLE 12

The same was repeated with an apparatus as shown in FIG. 1, with the automatic control, and the results obtained were in line with the above.

Having described the invention, modifications will be evident to those skilled in the art without departing from the spirit of the invention, as defined in the appended claims.

I claim:

1. A microwave vacuum oven for rapidly determining the volatile material content in samples susceptible to damage due to pyrolysis and heat degeneration comprising in combination: a vacuum chamber for receiving at least one open sample container containing at least one sample to be tested, and in combination therewith, a microwave source for rapidly liberating volatile material from said at least one sample, adjusting means for varying the energy emitted from said microwave source, a valve means connected to said chamber for alternatively creating a vacuum in said chamber or releasing from said chamber said vacuum, or releasing from said chamber said vacuum, means to detect the liberation of the volatile material out of said vacuum chamber, means to determine the rate of volatilization of said sample, means to convert said rate of volatilization as a signal, and to convey and sense said signal to a control means to determine said rate of volatilization of said at least one sample over time, and wherein (said adjusting means responsive to) said control means delivers an input to said adjusting means, whereby said adjusting means automatically varies the energy emitted from said microwave source, whereby upon vacuum conditions and initial heating the rate of volatilization decreases, and at near a point of inflection when said rate of volatilization decreases, said control means actuates said adjustment means to lower said microwave energy, while maintaining said vacuum in said chamber throughout until said means to detect liberation of the volatile material out of said vacuum chamber detects complete liberation of the volatile material out of said vacuum chamber, and thereafter releasing from said chamber, said vacuum with said valve means.

2. The microwave oven as defined in claim 1, wherein said vacuum chamber consists in two portions, said portions having walls susceptible to microwave radiation to liberate volatile materials from samples containing said volatile materials to be located within said vessel, said walls defining near the edges matching complementary lips for receiving the lips of the other of said portions, a thick deformable gasket having a gas passage means and in sealing engagement between the complementary matching lips of said portions, to form therewith a substantially leakproof chamber provided with said passage means for joining said means for alternatively selecting a vacuum or releasing said vacuum and wherein said portions are easily removable from each other.

3. The oven as defined in claim 1 wherein said means to determine the rate of volatilization of said sample is a weight sensing device for transmitting the weight of said at least one sample as a signal to said control means to automatically adjust microwave energy rate of the output whereby upon initial heating of a sample the weight decreases up to a point of inflection, and at said point the said control means actuates said adjustment means to lower the microwave energy.

4. The oven as defined in claim 1, wherein said means to determine the rate of volatilization of said sample is a vacuum sensing device to sense vacuum of said chamber, a means to translate and convey the sensed vacuum to said control means, said control means cooperating with said means of adjusting the energy output, to automatically adjust the microwave energy output of said microwave source whereby, upon initial heating of a sample, the vacuum decreases up to a point of inflection where the rate of volatilization of volatile material decreases, and at said point, when vacuum increases, said control means actuates said adjustment means to lower said microwave energy output to lower the microwave energy.

5. The oven as defined in claim 1, wherein said means to determine the rate of volatilization is a temperature sensing device to sense the temperature of said chamber, to automatically adjust the microwave energy output of said microwave source whereby, upon initial heating of a sample, the temperataure increases up to a point followed by a constant temperature until volatile material ceases to be delivered, and at said point, when the rate of which the temperature increases, the said control means actuates said adjustment means to lower said microwave energy output to a preset value.

6. A method for rapidly determining the volatile material content in a sample susceptible to damage due to pyrolysis and/or heat degradation comprising: (a) maintaining a vacuum environment around a sample containing volatile material, (b) subjecting said sample to selectively variable microwave radiation energy, to rapidly liberate the volatile material in said sample while measuring the rate of volatilization in said sample over time, (c) detecting a point of inflection at which said rate of volatilization decreases, (d) at said point decreasing the amount of radiation energy generated into said sample, while maintaining vacuum and continuing detecting the rate of volatilization, until said rate stops, indicative that said volatile material is completely liberated from said sample and (e) stopping the radiation energy at or near the point of inflection at which said volatile material is completely liberated from said sample while said vacuum is maintained until the environment surrounding said sample is substantially free from any volatile material liberated from said sample.

7. The method as defined in claim 6 wherein said microwave energy is gradually decreased as the rate of volatization decreases.

8. The method as defined in claim 6 wherein said decrease is step-wise.

9. The method as defined in claim 6 wherein said monitoring consists in recording over time at least one of the factors consisting of the vacuum and temperature, said at least one factor recorded over time characterized by a curve, generating a plateau or inflection whereby said radiation is immediately decreased upon the occurrence of said plateau or inflection point.

10. The method as defined in claim 6 wherein said rate of volatilization is obtained by constantly monitoring the rate at which the volatile material is liberated from the sample into the environment surrounding it.

11. The method as defined in claim 10 wherein said monitoring is performed by measuring the weight of said sample, said weight gradually decreasing over time up to a point where the ratio of weight over time levels off, and at said point immediately stopping said radiation.

12. The method as defined in claim 10 wherein said monitoring is performed by condensing the volatile material, liberated from said sample, at a temperature at which the vapour pressure of said volatile material is substantially low under said vacuum condition; the rate of accumulation of said volatile material indicative of the rate of liberation of volatile material.

* * * * *